United States Patent [19]

Wulff et al.

[11] 4,286,057
[45] Aug. 25, 1981

[54] METHOD AND REAGENT FOR THE DETERMINATION OF CREATINE KINASE

[75] Inventors: Karl Wulff, Weilheim; Fritz Stähler, Tutzing; Wolfgang Grüber, Tutzing-Unterzeismering, all of Fed. Rep. of Germany

[73] Assignee: Boehringer Mannheim GmbH, Sandhofer, Fed. Rep. of Germany

[21] Appl. No.: 125,381

[22] Filed: Feb. 28, 1980

[30] Foreign Application Priority Data

Mar. 2, 1979 [DE] Fed. Rep. of Germany ....... 2908054

[51] Int. Cl.³ .............................................. C12Q 1/66
[52] U.S. Cl. ......................................... 435/8; 435/17; 435/810
[58] Field of Search ............................. 435/8, 810, 17

[56] References Cited

U.S. PATENT DOCUMENTS

| | | | |
|---|---|---|---|
| 3,575,811 | 4/1971 | Chappelle et al. | 435/8 |
| 4,080,265 | 3/1978 | Antonik | 435/8 |

OTHER PUBLICATIONS

Lundin A. et al.; Clinica Chimica Acta, vol. 87, pp. 199-209, (1978).
Gates B. J. et al.; Archives of Biochemistry and Biophysics; vol. 169, pp. 616-621, (1975).
Lee R. T. et al.; Archives of Biochemistry and Biophysics, vol. 141, pp. 38-52; (1970).

*Primary Examiner*—Benoit Castel
*Attorney, Agent, or Firm*—Sprung, Felfe, Horn, Lynch & Kramer

[57] ABSTRACT

Creatine kinase is determined by the reaction of creatine phosphate with adenosine diphosphate with the formation of adenosine triphosphate, reaction of the latter with luciferin and oxygen in the presence of luciferase and diadenosine pentaphosphate with the formation of oxyluciferin and adenosine monophosphate, and measurement of the light thereupon emitted, the reaction being performed with a saturated concentration of adenosine diphosphate and substrate, in the presence of 1 to 10 millimoles per liter of AMP at pH values of 5.8 to 7.5, with at least 50 units of luciferase per test. It is desirable to operate in the presence of diadenosine pentaphosphate or sodium fluoride and a sequestering agent.

13 Claims, 3 Drawing Figures

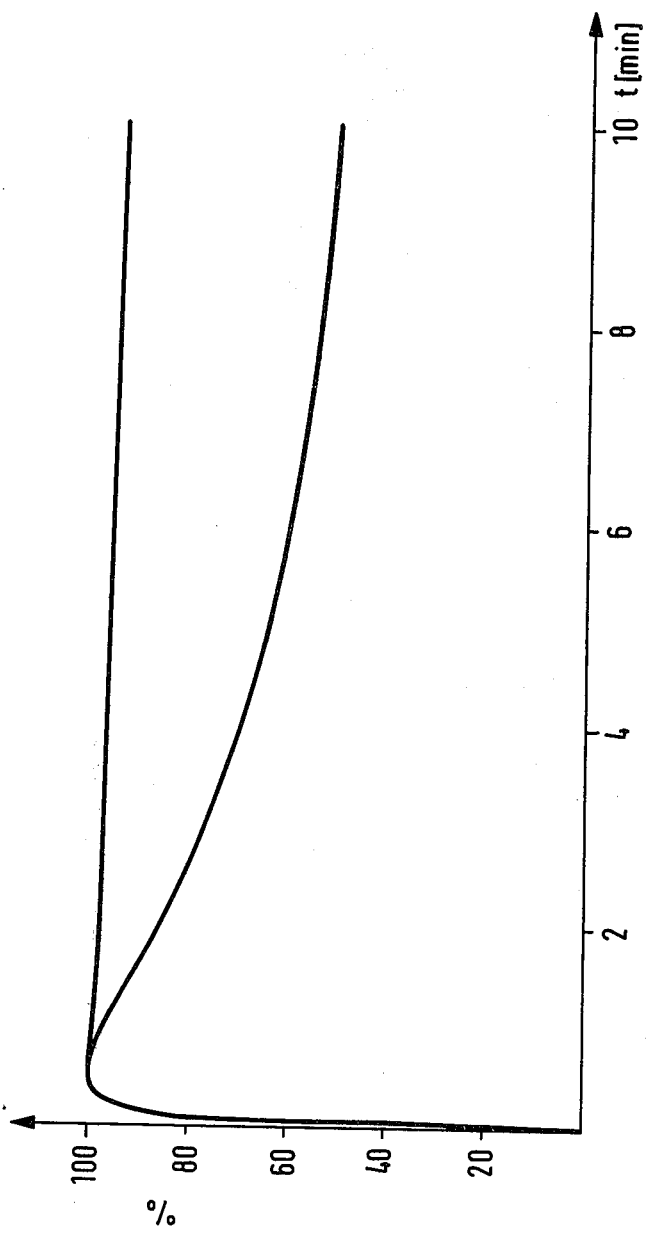

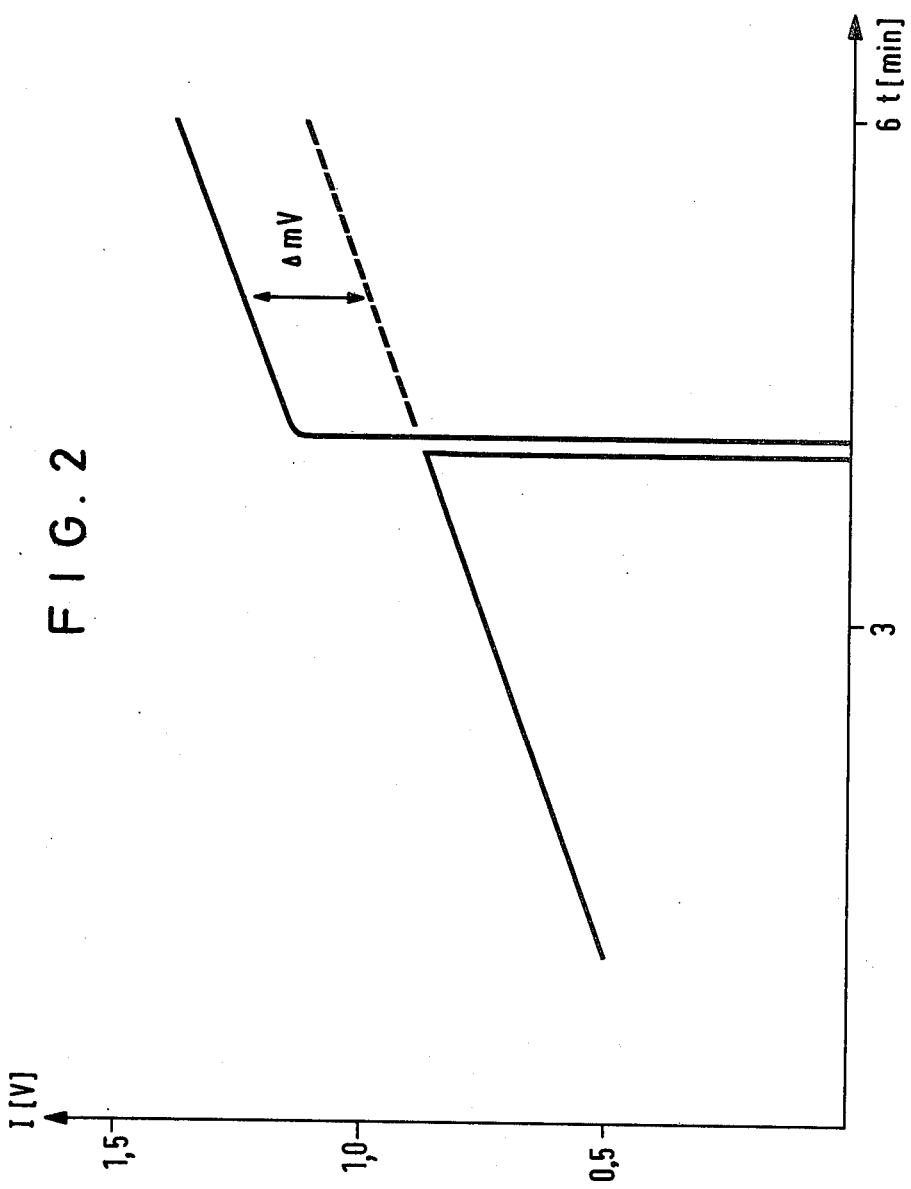

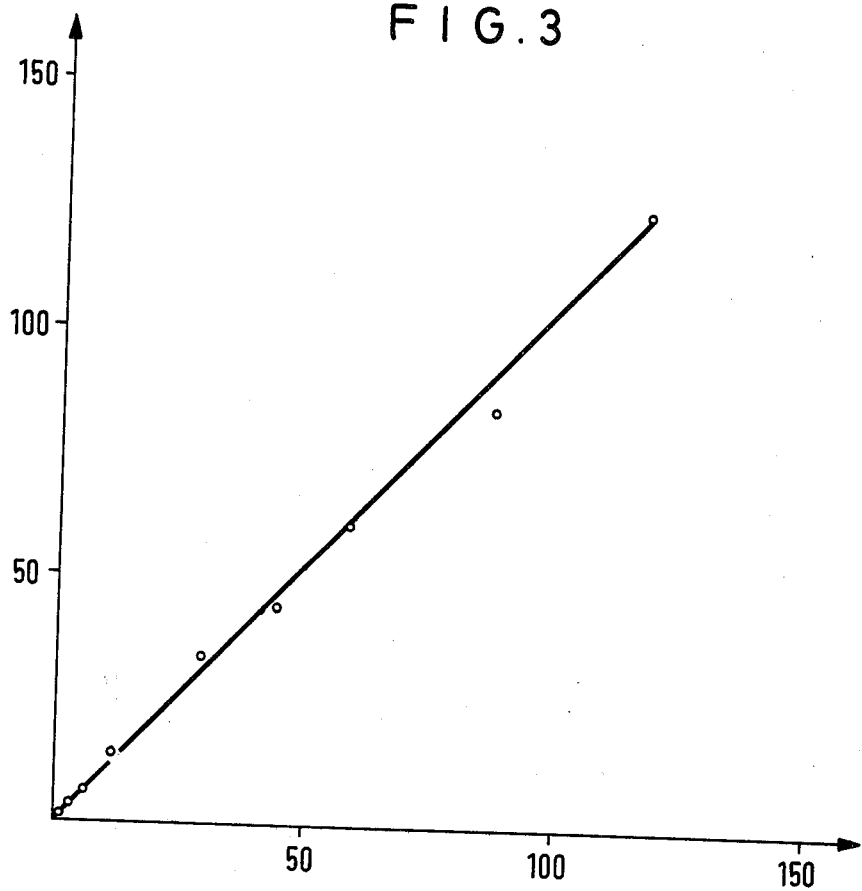

METHOD AND REAGENT FOR THE DETERMINATION OF CREATINE KINASE

BACKGROUND

The invention relates to a method and a reagent for the photometric determination of the activity of creatine phosphokinase (E.C. 2.7.3.2), hereinafter called CK, by means of the bioluminescent system of fireflies.

CK catalyzes the following reaction:

$$\text{ADP} + \text{creatine phosphate} \underset{}{\overset{CK}{\rightleftharpoons}} \text{ATP} + \text{creatine} \quad (1)$$

In the human body, two different kinds of sub-units of this enzyme occur, the sub-units M and B. Since the active enzyme is composed of two sub-units, and since the two sub-units can combine freely with one another, three types of enzyme are possible, the muscle type (CK-MM), the brain type (CK-BB) and the hybrid type (CK-MB), which occurs almost exclusively in the myocardium and enters into the serum in myocardial infarction, where it can be measured in an increased concentration. The activity of this isoenzyme, in addition to the total activity of CK in the serum, is of great importance in the diagnosis of myocardial infarction.

CK activity is commonly determined by an absorption photometry method in which the formation of ATP (cf. Equation 1) is measured in the following manner:

$$\text{ATP} + \text{D-Glucose} \underset{}{\overset{\text{hexokinase}}{\rightleftharpoons}} \text{ADP} + \text{D-Glucose-6-phosphate} \quad (2)$$

$$\text{D-glucose-6-phosphate} + \text{NADP}^+ \overset{\text{G-6-PDH}}{\longrightarrow} \text{D-gluconate-6-phosphate} + \text{NADPH} + \text{H}^+ \quad (3)$$

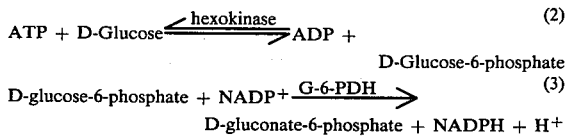

This determination of the CK activity by measuring the amount of ATP that has been formed is interfered with by the adenylate kinases (E.C. 2.7.4.3 "myokinases") of the serum (originating from the liver, muscles or erythrocytes), which catalyze the following reaction:

$$2\,\text{ADP} \underset{}{\overset{\text{myokinase}}{\rightleftharpoons}} \text{ATP} + \text{AMP} \quad (4)$$

Their activity can be most effectively inhibited by the addition of 5 to 10 millimoles per liter of adenosine-5'-monophosphate (AMP) and 10 micromoles per liter of diadenosine pentaphosphate (Ap5A), which eliminates their interference with the absorption photometry test. The interference can also be eliminated by using 1 to 10 millimoles per liter of NaF instead of Ap5A. An important disadvantage of these methods is a lag phase which cannot be reduced to less than 90 seconds. Another important disadvantage of the absorption photometry method lies in its poor sensitivity, which permits the measurement only of activities above 10 units per liter, and therefore makes it virtually impossible to measure the CK-MB activity, particularly in the low pathological range, as well as in the normal range.

Consequently a number of attempts have been made to detect the formation of ATP by CK through the luciferase bioluminescence of the firefly. This method has the advantage of greater sensitivity and the absence of the lag phase.

The luciferase of the firefly (Photinus pyralis et al.) catalyzes the following reaction:

$$\text{ATP} + \text{luciferin} + \text{O}_2 \overset{\text{luciferase}}{\longrightarrow} \text{oxyluciferin} + \text{CO}_2 + \text{AMP} + \text{PP}_i + \text{light} \quad (5)$$

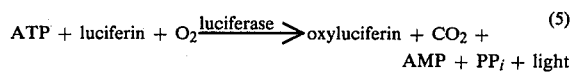

The light that is produced in this reaction is emitted with a yield of virtually 1 Einstein per mole of ATP. It has a wavelength of 562 nm at the peak. The reaction is extremely sensitive, and permits the quantitative determination of ATP concentrations down to $10^{-13}$ moles per liter.

It is known, however, that the firefly Reaction 5 is so greatly inhibited by AMP (Arch. Biochem. Biophys. 141, 49, 1970) that the practical application of this reaction in the measurement of CK activities in accordance with Equation 1 in the serum is very problematical, since it prevents the use of AMP as an inhibitor of the adenylate kinase in Reaction 4 (Proc. Nat. Acad. Sci. 71, 1384 to 1387 (1974)). It is furthermore known to partially eliminate the necessity of the inhibition of adenylate kinase by performing the reaction (1) at a sub-optimal ADP concentration, that is, without substrate saturation, and thus operating at a substrate concentration at which, on account of the rather steep curve representing the activity of adenylate kinase in relation to the substrate concentration, the activity of the adenylate kinase is negligibly small in comparison to that of the CK. In this manner, the CK in the serum can be measured along with the adenylate kinase by the bioluminescent method (Clin. Chim. Acta 87, 199 to 209 (1978)), but, of course, considerable disadvantages must be accepted:

1. The CK reaction no longer is performed on the basis of a pseudo zero order.
2. The recovered CK activity, with respect to an internal calibration with ATP, amounts to only about 11% of the values measured by the absorption photometry test.
3. Slight inaccuracies in the ADP concentration have a very great effect on the results.

THE INVENTION

The present invention, therefore, is addressed to the problem of creating a bioluminescent test method for the determination of CK activity, which will not have these disadvantages, and in which especially:

1. The adenylate kinases can be completely inhibited,
2. The activity measured by means of bioluminescence expressed in I.U. (micromoles of substrate transformation per minute) is equal to the activity measured in the mixture used in the absorption photometry, and
3. The procedure can be performed with the CK saturated with the substrate.

The method of the invention for the determination of creatine kinase by the reaction of creatine phosphate with adenosine diphosphate with the formation of adenosine triphosphate, the reaction of the latter with luciferin and oxygen in the presence of luciferase and diadenosine pentaphosphate with the formation of oxyluciferin and adenosine monophosphate, and the measurement of the light thus emitted, is characterized in that the reaction is performed with the adenosine diphosphate as substrate in a saturated concentration, in the presence of 1 to 10 millimoles per liter of AMP, at pH values of 5.8 to 7.5, with at least 50 units of luciferase per test.

Under the above-stated conditions, surprisingly, not only are the adenylate kinases completely inhibited, but the luciferase reaction takes place according to a pseudo first order, while inhibition by AMP does not manifest itself disadvantageously.

Preferably the process of the invention is performed at a pH between 6.3 and 7.2, especially preferably between pH 6.5 and 6.9. The ADP concentration per test amounts preferably to 0.1 to 10 millimoles per liter; the concentration of diadenosine pentaphosphate (Ap5A) amounts preferably to 1 to 100 micromoles per liter.

In the above-stated preferred pH range, the best results are obtained in the presence of 0.5 to 2 millimoles per liter of ADP, 5 to 50 micromoles per liter of Ap5A, and 5 to 10 millimoles per liter of AMP.

In addition to the reagents specified above, it is preferable in the process of the invention also to add an organic sulfohydryl compound. Suitable sulfohydryl compounds are, for example, N-acetylcysteine, dithiothreitol, dithioerythritol, and reduced glutathione. N-acetylcysteine is used preferentially. It is furthermore desirable to add a sequestering agent, such as ethylene diamine tetraacetic acid (EDTA), Trilone, Komplexone, Sequestrene and the like. Also desirable is the addition of stabilizers, such as serum albumin, in amounts familiar to the technician for the stabilization of enzymatic reagents.

In the firefly reaction, the intensity of the emitted light is directly proportional to the concentration of the ATP. The measured magnitude is tantamount to the rate of the reaction. For a reaction of the pseudo-first order ($c_{ATP} << K_m$) the following applies:

$$I = \frac{d(h \cdot v)}{dt} = \frac{V_{max}}{K_m} \cdot c_{ATP}$$

If this reaction is preceded by a reaction yielding ATP, such as the CK reaction for example, then:

$$\frac{d\,c_{ATP}}{dt} \sim \frac{d\,I}{dt}$$

i.e., the result is a linear increase of the light intensity, the rate of which should be proportional to the activity of the CK.

These enzymokinetic considerations are based on the assumption that the activity of luciferase does not vary within the period of observation. This, however, is normally not the case, since the firefly reaction is subject to a product inhibition by oxyluciferin, which in the measurement of a defined ATP concentration results in a sharp decrease of the signal with time, and thus leads to a rather flash-like signal-time curve which is constant for no more than a few seconds.

But it has surprisingly been found that the AMP which is added in accordance with the invention for the inhibition of the adenylate kinases so modifies the properties of the firefly luciferase under the stated conditions, that the product inhibition by oxyluciferin which usually occurs in the course of the reaction is eliminated. The result is that, when a defined ATP concentration is measured, instead of the flash-like signal-time curve, as heretofore, a substantial constancy of signal over more than 15 minutes is achieved.

In the appended drawing, FIG. 1 shows the constancy of signal achieved in accordance with the invention. It was achieved with the following test mixture:

| Component | |
| --- | --- |
| D-luciferin | 35 (μmol/l) |
| luciferase | 400 units |
| | (units per test) |
| trisacetate buffer | pH 7.75, 100 mmol/l |
| EDTA | 2 mmol/l |
| Mg++ | 10 mmol/l |
| ATP | $10^{-8}$ mol/l |
| RSA | 0.1% |
| AMP | 5 mmol/l |

Additional subject matter of the invention is a reagent for the determination of creatine kinase. This reagent is characterized by containing 10 to 500 micromoles of luciferin, at least 50 units of luciferase, 5 to 250 millimoles of buffer, pH 5.8 to 7.5, 1 to 10 millimoles of AMP, 0.1 to 10 millimoles of ADP, 1 to 100 micromoles of diadenosine pentaphosphate, 5 to 50 millimoles of creatine phosphate, 1 to 100 millimoles organic sulfohydryl compound, 0.1 to 5 millimoles of sequestering agent, 0.05 to 1 wt.-% of bovine serum albumin and 1 to 100 millimoles of magnesium ions per liter of test solution. It can be in solid or dissolved form.

In a preferred embodiment, the reagent of the invention contains 15 to 50 micromoles of luciferin, 1000 to $5 \times 10^5$ units of luciferase, 60 to 120 millimoles of buffering substance, pH 6.3 to 7.2, 5 to 10 millimoles of AMP, 0.5 to 2 millimoles of ADP, 5 to 50 micromoles of diadenosine pentaphosphate, 20 to 40 millimoles of creatine phoshate, 2 to 50 millimoles of organic sulfohydryl compound, 0.5 to 3 millimoles of sequestering agent, 0.05 to 0.2 wt.-% of bovine serum albumin, and 5 to 20 millimoles of magnesium ions, for each liter of test solution.

As the sequestering agent, the reagent of the invention preferably contains EDTA, and it contains N-acetylcysteine as the preferred sulfohydryl compound.

Examples of suitable buffer substances are tris-acetate, imidazole acetate, hepes as acetate, hepes as sulfate or chloride, tris imidazol, tra as sulfate or chloride, arsenate or phosphate buffer. Glycine buffer is also suitable in the stated range. Imidazole acetate and hepes acetate are used perferentially.

EXAMPLES

The following examples will further explain the invention. The concentrations given relate to the prepared reagent solution used in the test; the quantities indicate the amount needed for the preparation of one liter of test solution. In the examples, a firefly luciferase was used which was isolated by the method described in FEBS-Lett. 70, 167 to 170 (1976). The luciferin was in each case a commercially available product of the highest purity obtainable, such as for example Sigma lots 58C-0349 and 98C-3942, or Calbiochem lot 540022. Other luciferin preparations of comparable purity are likewise suitable.

The luciferase units specified hereinbelow were determined as follows:

| Test Mixture | Final Concentration in Test |
| --- | --- |
| D-luciferin | 35 micromoles per liter |
| tris-acetate, pH 7.75 | 100 millimoles per liter |

-continued

| Test Mixture | Final Concentration in Test |
| --- | --- |
| EDTA | 2 millimoles per liter |
| RSA | 0.1% |
| (Mg$^{++}$) | 10 millimoles per liter |
| luciferase | variable |
| ATP (as a start) | $2.5 \times 10^{-7}$ moles per liter |

The measurement was performed in a commercial ATP photometer (Mfr., SAI, San Diego, Calif., U.S.A.)

The enzyme unit is the amount which under the above-described conditions gives a signal of 37 pulses in ten seconds, the sensitivity potentiometer on the above apparatus being set at 6.7.

EXAMPLE 1

| Solutions | Conc. in Solution | Conc. in Test |
| --- | --- | --- |
| Solution 1 | | |
| EDTA | 4 mmol/l | 2 mmol/l |
| Mg-acetate | 20 mmol/l | 10 mmol/l |
| D-luciferin | 70 μmol/l | 35 μmol/l |
| luciferase | 400 units/ml | 400 units/test |
| RSA | 4 g/l | 0.2% |
| imidazole acetate, pH 6.7 | 110 mmol/l | 100 mmol/l |
| Solution 2 | | |
| AMP | 33 mmol/l | 10 mmol/l |
| N-acetylcysteine (NAC) | 33 mmol/l | 10 mmol/l |
| Ap5A | 33 μmol/l | 10 μmol/l |
| ADP | 3.3 mmol/l | 1 mmol/l |
| imidazole acetate, pH 6.7 | 110 mmol/l | 100 mmol/l |
| Solution 3 | | |
| creatine phosphate | 300 mmol/l | 30 mmol/l |
| imidazole acetate | 110 mmol/l | 100 mmol/l |
| Solution 4 | | |
| ATP | $5 \times 10^{-4}$ mol/l | $5 \times 10^{-6}$ mol/l |

Test

The following are combined:
1000 microliters of solution 1
600 microliters of solution 2
200 microliters of serum sample The mixture is preincubated at 25° C. for 5 minutes, and then the test glass is placed in the measuring instrument (SAI Photometer), and the reaction is started by adding 200 microliters of solution 3, which has also been preincubated at 25° C. The curve is traced on a recorder and, after about 2 minutes the internal calibration of micromoles of substrate transformation per minute is performed with 20 microliters of Solution 4. The results are automatically traced by a recorder. The curve is traced for an additional 2 or 3 minutes to obtain a graph that is easy to analyze, and which is shown in FIG. 2 of the appended drawing.

The linearly rising curve gives the rate of rise in arbitrary scale divisions per minute, and the calibration stage permits the conversion of scale divisions (entered as ΔmV) in micromoles of ATP. The curve obtained by the conversion is represented in FIG. 3 of the drawing.

EXAMPLE 2

Test kit for 100 tests.

Bottle 1 contains:
  0.4 millimoles EDTA
  2 millimoles magnesium acetate
  7 micromoles luciferin
  $4 \times 10^4$ units luciferase
  400 mg bovine serum albumin
  11 millimoles imidazole buffer, pH 6.7 as lyophilizate.
Bottle 2 contains:
  2 millimoles adenosine-5'-monophosphate
  2 millimoles N-acetylcysteine
  2 micromoles diadenosine pentaphosphate
  0.2 millimoles adenosine-5'-diphosphate
  6.5 millimoles imidazole acetate buffer, pH 6.7 as lyophilizate.
Bottle 3 contains:
  6 millimoles creatine phosphate
  2.2 millimoles imidazole acetate buffer, pH 6.7 as lyophilizate.
Bottle 4 contains:
  $10^{-6}$ moles ATP as lyophilizate.

The content of bottle 1 is dissolved in 100 ml of water, those of bottle 2 in 60 ml of water, those of bottle 3 in 20 ml of water and those of bottle 4 in 2 ml of water for the preparation of ready-to-use solutions. The test is performed as in Example 1, using the amounts of the individual solutions which are given in Example 1.

It will be understood that the specification and examples are illustrative, but not limitative of the present invention and that other embodiments within the spirit and scope of the invention will suggest themselves to those skilled in the art.

What is claimed is:

1. In a method for the determination of creatine kinase by the reaction of creatine phosphate with adenosinediphosphate with the formation of adenosine triphosphate, transformation of the latter with luciferin and oxygen in the presence of luciferase and diadenosine pentaphosphate with the formation of oxyluciferin and adenosine monophosphate, and measurement of the light emitted thereby, the improvement comprising performing the reaction at adenosine diphosphate substrate saturation concentration in the presence of 1 to 10 millimoles per liter of AMP, at pH values of 5.8 to 7.5, with at least 50 units per test of luciferase.

2. Improvement as claimed in claim 1 wherein 0.1 to 10 millimoles per liter of ADP and 1 to 100 micromoles per liter of diadenosine pentaphosphate are added.

3. Improvement as claimed in claim 2 wherein 0.5 to 2 millimoles per liter of ADP and 5 to 50 micromoles per liter of diadenosine pentaphosphate and 5 to 10 millimoles per liter of AMP are used and a pH of 6.2 to 7.2 is utilized.

4. Improvement as claimed in claim 1 wherein said determination is performed in the presence of a sequestering agent.

5. Improvement as claimed in claim 4 wherein the sequestering agent is ethylene diamine tetraacetic acid.

6. Improvement as claimed in claim 1 wherein said determination is performed in the presence of an organic sulfohydryl compound.

7. Improvement as claimed in claim 6 wherein said organic sulfohydryl compound is N-acetyl cysteine.

8. Improvement as claimed in claim 1 wherein the determination is performed in the presence of serum albumin.

9. Reagent for the determination of creatine kinase comprising
  10 to 500 micromoles of luciferin,
  at least 50 units of luciferase,
  5 to 250 millimoles of buffer substance, pH 5.8 to 7.5,
  1 to 100 micromoles of diadenosine pentaphosphate,
  1 to 10 millimoles of AMP,
  5 to 50 millimoles of creatine phosphate,
  0.1 to 10 millimoles of ADP, 1 to 100 millimoles of organic sulfohydryl compound,
0.1 to 5 millimoles of sequestering agent,
0.05 to 1 weight percent of bovine serum albumin, and
1 to 100 millimoles of magnesium ions for every one liter of test solution.

10. Reagent as claimed in claim 9 comprising
15 to 50 micromoles of luciferin,
100 to $5 \times 10^4$ units of luciferase,
60 to 120 millimoles of buffer substance,
6.3 to 7.2 pH,
5 to 10 millimoles of AMP,
0.5 to 2 millimoles of ADP,
5 to 50 micromoles of diadenosine pentaphosphate,
20 to 40 millimoles of creatine phosphate,
2 to 50 millimoles of organic sulfohydryl compound,
0.5 to 3 millimoles of sequestering agent,
0.05 to 0.4 weight percent of bovine serum albumin, and
5 to 20 millimoles of magnesium ions for every one liter of test solution.

11. Reagent as claimed in claim 9 also containing ethylene diamine tetraacetic acid as a sequestering agent.

12. Reagent as claimed in claim 9 containing N-acetyl cysteine as a sulfohydryl compound.

13. Reagent as claimed in claim 9 also containing imidazole acetate or hepes acetate as a buffer substance.

* * * * *